United States Patent [19]
Van Schoiack et al.

[11] Patent Number: 5,599,460
[45] Date of Patent: Feb. 4, 1997

[54] WATER/GLYCOL SENSOR FOR USE IN OIL SYSTEMS

[76] Inventors: Michael Van Schoiack, 6825 176th Ave. NE., Ste. 100, Redmond, Wash. 98052; Peter von der Porten, 1902 Matthews Avenue, Vancouver, BC., Canada, V6J 2T7

[21] Appl. No.: 106,359

[22] Filed: Aug. 13, 1993

[51] Int. Cl.⁶ .................................................. B01D 35/14
[52] U.S. Cl. ........................ 210/746; 210/801; 210/804; 210/85; 210/306; 210/311; 184/6.24; 184/108; 73/61.43
[58] Field of Search ................ 210/85, 96.1, 746, 210/DIG. 5, 168, 305, 306, 311, 799–801, 804; 184/6.24, 108; 73/61.43

[56] References Cited

U.S. PATENT DOCUMENTS

| | | | |
|---|---|---|---|
| 1,787,577 | 1/1931 | Hills | 210/301 |
| 2,349,992 | 5/1944 | Schrader | 175/183 |
| 3,670,319 | 6/1972 | Ohtani | 340/244 |
| 4,112,744 | 9/1978 | Tassano | 73/61.43 |
| 4,257,890 | 3/1981 | Hurner | 210/112 |
| 4,372,847 | 2/1983 | Lewis | 210/86 |
| 4,425,239 | 1/1984 | Jacocks et al. | 10/787 |
| 4,437,986 | 3/1984 | Hutchins et al. | 210/130 |
| 4,475,498 | 10/1984 | Hurner | 123/198 |
| 4,502,955 | 3/1985 | Schaupp | 210/149 |
| 4,510,051 | 4/1985 | Diry | 210/94 |
| 4,594,892 | 6/1986 | Asmundsson | 73/304 |
| 4,609,458 | 9/1986 | Okamura et al. | 210/85 |
| 4,624,779 | 11/1986 | Hurner | 210/180 |
| 4,745,893 | 5/1988 | Atherton et al. | 123/196 |
| 4,806,847 | 2/1989 | Atherton et al. | 324/61 |
| 4,872,316 | 10/1989 | Browne et al. | 62/129 |
| 4,873,489 | 10/1989 | Melcher et al. | 324/453 |
| 4,876,016 | 10/1989 | Young et al. | 210/739 |
| 4,888,989 | 12/1989 | Homer | 73/304 |
| 4,959,965 | 10/1990 | Browne et al. | 62/129 |
| 4,961,845 | 10/1990 | Dawson et al. | 210/85 |
| 4,967,880 | 11/1990 | Krambs | 184/6.4 |
| 4,995,992 | 2/1991 | Hurner | 210/803 |
| 5,055,794 | 10/1991 | Kawashima | 324/453 |
| 5,274,335 | 12/1993 | Wang et al. | 324/689 |

*Primary Examiner*—Matthew O. Savage
*Attorney, Agent, or Firm*—Glenn D. Bellamy; Teresa J. Wiant

[57] ABSTRACT

The present invention provides a sensor (10) and method for detecting the presence of water or glycol in an oil system. The water/glycol sensor includes a water/glycol concentrator (12) which concentrates the water and glycol in a concentrating zone (84). A water/glycol detection probe (14) is located in the concentration zone (84) such that minute quantities of water or glycol in the system may be detected.

4 Claims, 5 Drawing Sheets

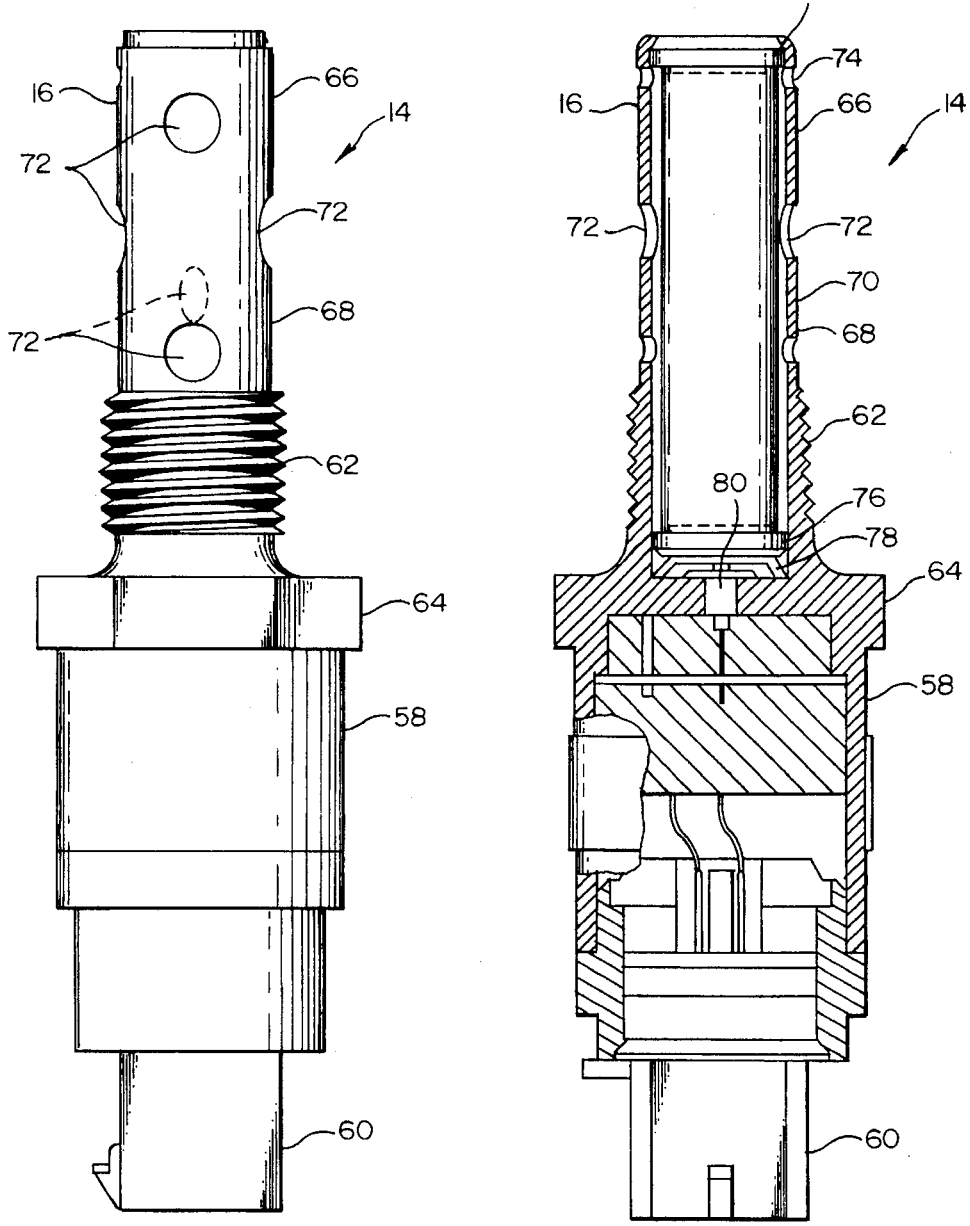
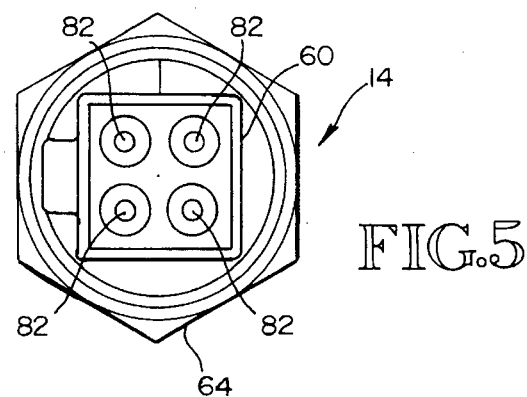
FIG.3
FIG.4
FIG.5

5,599,460

WATER/GLYCOL SENSOR FOR USE IN OIL SYSTEMS

TECHNICAL FIELD

This invention relates to a sensor for detecting the presence of minute quantities of water/glycol in an oil system, such as for lubrication oil, fuel oil or hydraulic oil.

BACKGROUND OF THE INVENTION

Many devices, electronic or otherwise, have been made for the purpose of detecting the presence of water/glycol in an oil system. The presence of water/glycol in an oil system is significant not only because it is a contaminant, but also because its presence is often an indication that coolant is leaking due to system damage. The detection of engine or pump damage at the earliest possible stage can significantly reduce the cost of repair. This is especially important on very expensive heavy machinery such as is used in construction or mining.

U.S. Pat. No. 4,624,779, issued Nov. 25, 1986, and U.S. Pat. No. 4,995,992, issued Feb. 26, 1991, both to Irwin E. Hurner, disclose devices for filtering contaminants and water from fuel. These devices separate water by use of a microscreen and accumulate the separated water in a chamber to be drained away as necessary. U.S. Pat. No. 4,745,893, issued May 24, 1988, to Atherton et al. discloses an oil level sensor which includes a probe having a pair of electrodes forming a capacitor. This device digitally senses oil level by sensing the difference in capacitance between oil and air. The above-identified patents should be carefully studied and considered for placing the present invention in proper context.

SUMMARY OF THE INVENTION

The present invention is directed toward an apparatus for detecting the presence of water/glycol in oil. The apparatus comprises a concentrator and a water/glycol detection probe. The concentrator has a concentrating zone into which water/glycol from an oil and water/glycol mixture is concentrated. The detection probe is positioned in the concentrating zone. When an oil and water/glycol mixture is passed through the concentrator, the water/glycol is concentrated in the concentrating zone and the detection probe is operated to sense the presence of water/glycol in the concentrating zone.

In a preferred form of the invention, the concentrator comprises a chamber having an inlet and an outlet with a filter-separator operatively disposed in the chamber between the inlet and the outlet. The chamber includes the water/glycol concentrating zone into which moisture from the filter-separator is directed. The detection probe comprises a pair of electrodes forming a capacitor and may include orifices permitting oil or moisture to enter into a space between the electrodes. The apparatus further includes means responsive to the capacitance of the capacitor for signaling the presence of water/glycol in the oil. The capacitance is a function of the amount of water or glycol in the oil.

In another preferred form of the invention, the water/glycol detection probe includes a circuit which has a comparator to monitor the capacitance of the capacitor. The responsive means includes a warning system which is connected to the probe circuit. The warning system signals an increase in capacitance of the capacitor when water or glycol is present in the concentrating zone of the concentrator. The apparatus is particularly useful when the oil is part of an engine lubrication system.

The present invention further comprises a method for sensing the presence of water or glycol in an oil system. The method comprises providing a concentrator for concentrating water/glycol from an oil and water/glycol mixture. The oil and water/glycol mixture are passed through the concentrator such that the water/glycol is concentrated in a concentrating zone of the concentrator. A water/glycol detection probe is provided and positioned in the concentrating zone. The detection probe is operated to sense the presence of water/glycol in the concentrating zone. In a preferred form of the method, a warning system is provided. The detection probe signals the warning system when the detection probe indicates the presence of water or glycol in the system.

BRIEF DESCRIPTION OF THE DRAWINGS

Like reference numerals are used to indicate like parts throughout the various figures of the drawing, wherein:

FIG. 3 is a plan view of a water/glycol detecting probe according to the preferred embodiment of the present invention;

FIG. 4 is a sectional view of the probe shown in FIG. 3;

FIG. 5 is an end view of the probe shown in FIG. 3;

BEST MODE FOR CARRYING OUT THE INVENTION

The present invention provides a water/glycol sensor for use in oil systems, such as fuel systems, hydraulic systems, and lubrication systems. The sensor of the present invention detects the presence of water or glycol in the oil by measuring the capacitance between two electrodes of a capacitor immersed in oil. Glycol refers to ethylene glycol, which is widely used in combination with water as an antifreeze or coolant. As used herein, water/glycol refers to water, glycol or a mixture of the two, regardless of proportion.

The capacitance of a capacitor is related to the dimensions of the capacitor and the dielectric of the material between the electrodes of the capacitor according to the following formula:

$$C = \frac{KA}{d}$$

where C is the capacitance; K is the dielectric constant of the material between the electrodes of the capacitor; A is the area of the electrodes of the capacitor; and d is the distance between the electrodes of capacitor. In the system of the present invention, the area of the electrodes (A) and the distance between the electrodes (d) remains substantially constant. The capacitance is directly proportional to the dielectric constant of the material between the electrodes of the capacitor. The dielectric constants of water and glycol are significantly higher than the dielectric constant of oil.

This relationship, as it applies to the present invention, will be discussed in greater detail below.

Figure 1:
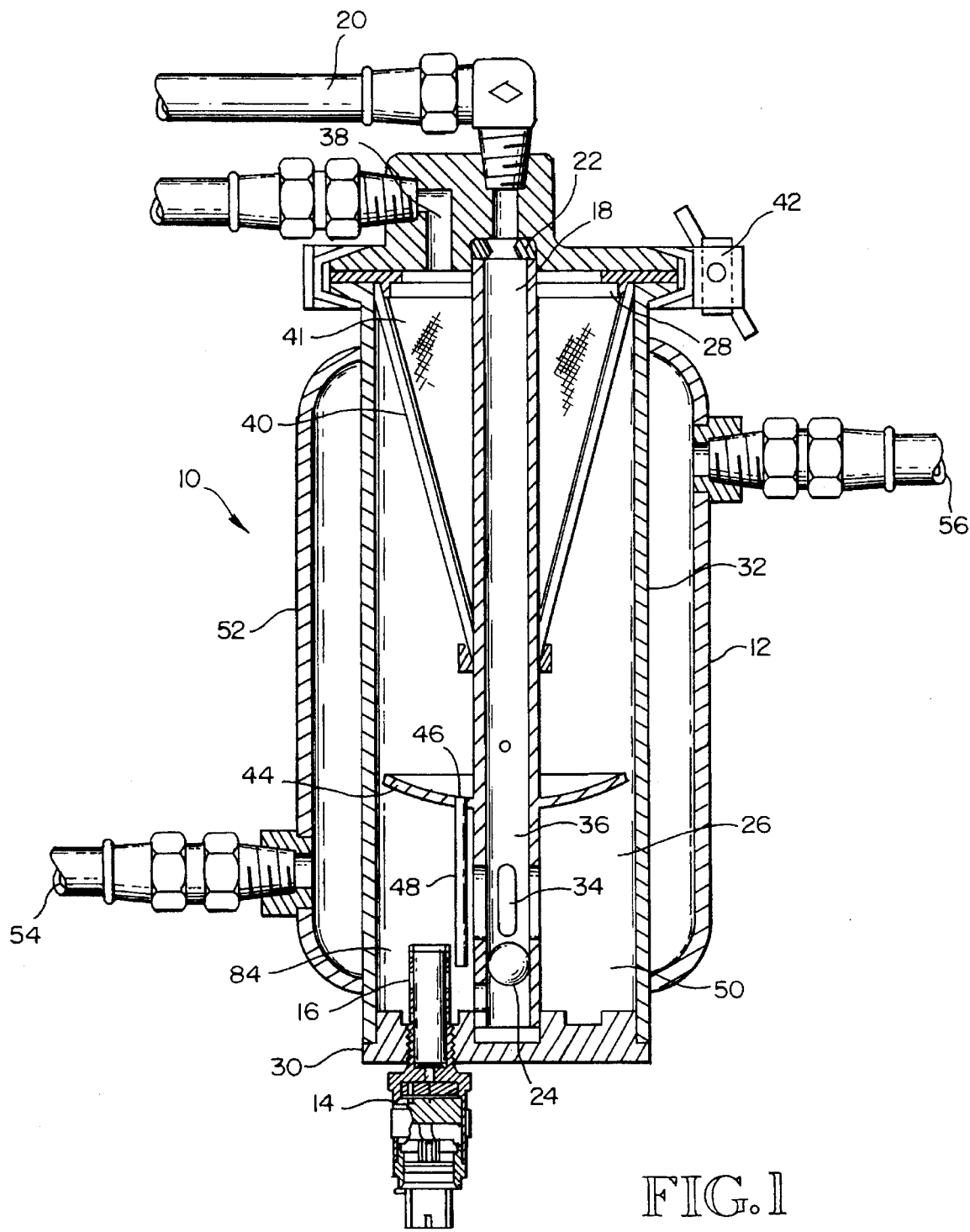
FIG. 1 is a sectional view of a device made in accordance to the preferred embodiment of the present invention.
Figure 2:
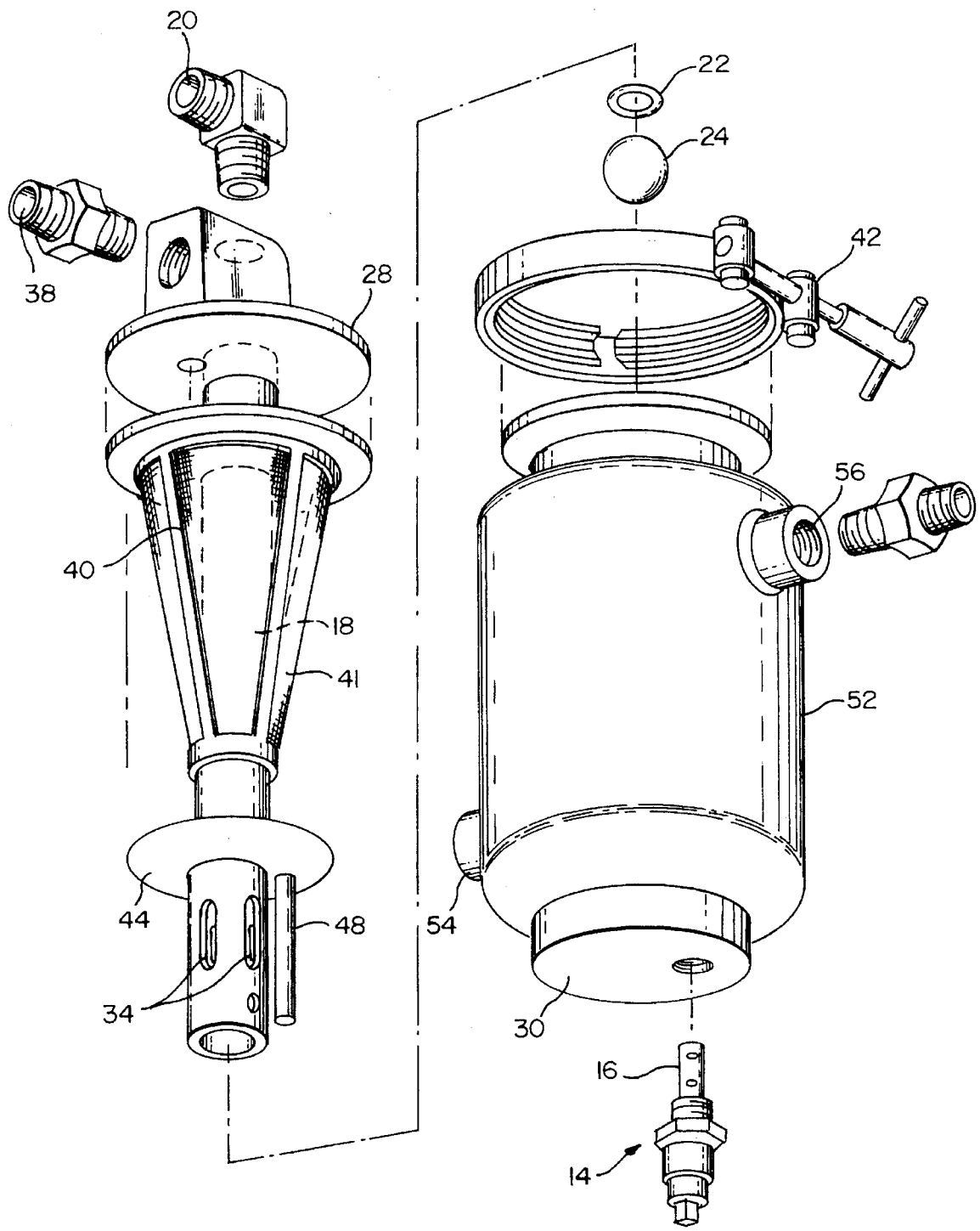
FIG. 2 is an exploded isometric view of the embodiment shown in FIG. 1.

As shown in FIGS. 1 and 2, the water/glycol sensor 10 of the present invention comprises a concentrator 12 and a water/glycol detection probe 14 which includes a capacitor 16. The concentrator 12 is preferably of the type described in U.S. Pat. No. 4,995,992 (issued Feb. 26, 1991), the disclosure of which is hereby incorporated by reference. The concentrator 12 has a first conduit 18 which is in communication with an entrance conduit 20. An o-ring 22 and a buoyant ball valve 24 are located in the first conduit 18. The O-ring 22 and buoyant ball valve 24 are sized for sealing the sensor 10 from an oil system when the sensor 10 is not in use.

A separator chamber 26 surrounds the first conduit 18. The separator chamber 26 is defined by a top wall 28, a bottom wall 30, and a sidewall 32. The first conduit 18 is in communication with the separator chamber 26 by slots 34 defined in a lower region 36 of the first conduit 18. An exit conduit 38 is located at one end of the separator chamber 26, behind a filter-separator 40. The filter-separator 40 includes a fine mesh screen 41. The top wall 28, filter-separator 40, and O-ring 22 are secured in place by a clamping structure 42. A spreader 44 is located in the separator chamber 26, above the slots 34. The spreader 44 forms a drain orifice 46 which is connected to a collection conduit 48 which extends into a lower region 50 of the separator chamber 26.

The separator chamber 26 is surrounded by a water jacket 52. The water jacket 52 includes an inlet 54 and an outlet 56. Preferably, the inlet 54 is in communication with the water from a cooling system of an engine.

As illustrated in FIG. 1, the water/glycol detection probe 14 extends through the bottom wall 30 into the lower region 50 of the separator chamber. The probe 14 is preferably of the type illustrated in U.S. Pat. No. 4,745,893 (issued May 24, 1988), the disclosure of which is hereby incorporated by reference. Referring to FIG. 3, the probe 14 has a body portion 58 which includes a connector 60. Screw threads 62 and wrench flats 64 are formed on an outer surface 66 of the probe. A front portion 68 of the outer surface 66 forms a first electrode 70 for the capacitor of the probe, as shown in FIG. 4. A plurality of orifices 72 are formed in the first electrode 70. A second cylindrical electrode 74 is disposed inside of the first electrode 70. A pair of insulating disks 76 support the second electrode 74, one at each end. Preferably, the insulating disks are composed substantially of ceramic. A belleville 78 washer is disposed between the first electrode 70 and the second electrode 74 to prevent vibration of the second electrode 74. A conductor 80 passes through a central opening in the washer 78. The conductor 80 interconnects the second electrode 74 with circuitry on the probe 14. Another conductor interconnects the first electrode 70 with the circuitry. Four pins 82 connect the circuitry to a warning system.

Figure 6:
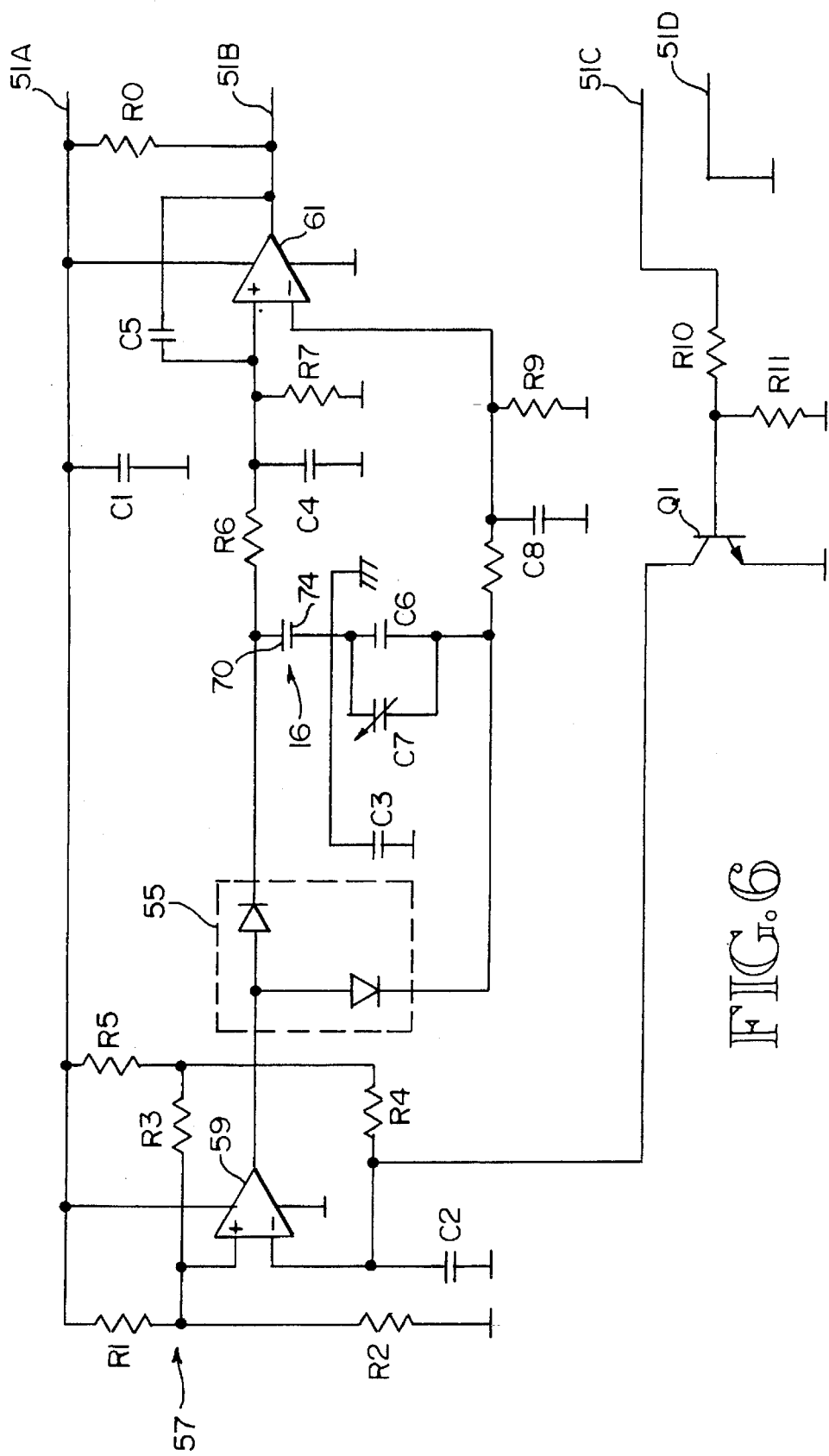
FIG. 6 is an electrical schematic of the circuitry of the probe of FIG. 3.
Figure 7:
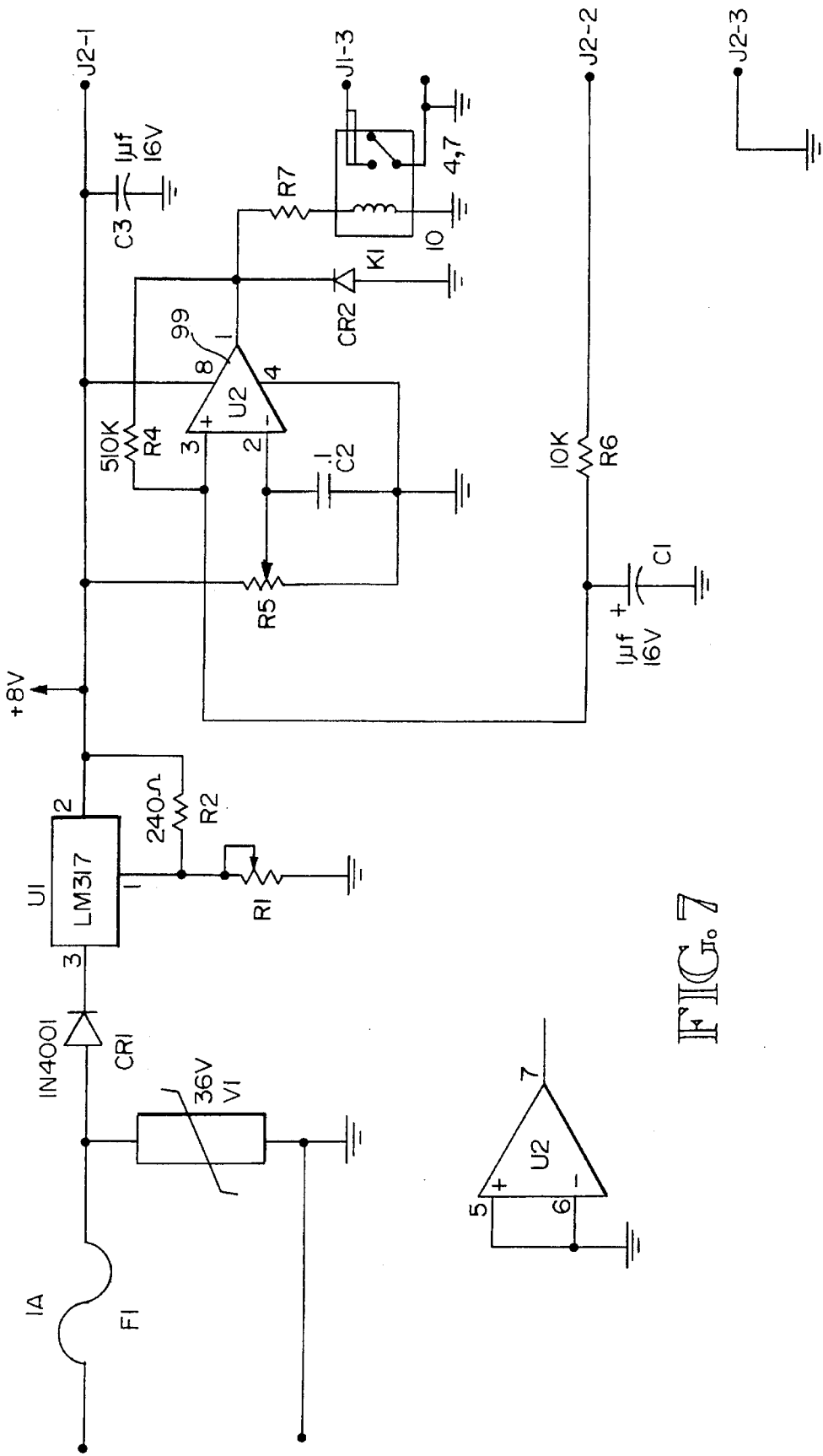
FIG. 7 is an electrical schematic of the circuitry of the system responsive to signals from the probe to indicate the presence of water/glycol in oil.

The probe circuitry is illustrated in FIG. 6. The circuitry of the warning system is illustrated in FIG. 7. The circuitry of both FIGS. 6 and 7 are designed for detecting the difference in the higher capacitance of the capacitor of a water/glycol contaminated oil compared to oil alone. The circuitry relays a signal of the high capacitance to an operator of the system.

In use, oil flows into the sensor 10 through the entrance conduit 20 and the first conduit 18, pushing the buoyant ball valve 24 away from the O-ring 22 and into the lower region 36 of the first conduit, as illustrated in FIG. 1. The oil passes out of the first conduit 18 through the slots 34 and fills the separator chamber 26, including the lower region 50 of the chamber which surrounds the probe 14. Oil enters into the probe 14 through the orifices 72 and fills the space between the electrodes 70, 74. The concentrator 12 is operated at a given high pressure such that the oil is forced through the fine mesh screen 41 of the filter-separator 40 and water or glycol collects on the surface of the screen and falls downwardly onto the spreader 44. This separation is facilitated by a difference between the surface tension of oil and water/glycol. At a given temperature and pressure, oil will pass through the fine mesh of the screen 41 while water/glycol will not and is shed away by the screen 41. From the spreader 44, the water or glycol passes through the drain orifice 46 in the spreader 44, through the collection conduit 48, and into a water/glycol concentrating zone 84 of the separator in the lower region 50 of the separator chamber.

If water or glycol is not present in the oil, the space between the electrodes 70, 74 of the capacitor is filled only with oil which results in a low capacitance across the capacitor. If water or glycol is present in the oil, the water or glycol is concentrated in the water/glycol concentrating zone 84 of the separator. The water or glycol enters the probe 14 through the orifices 72 and fills the space between the electrodes 70, 74. As the amount of water or glycol increases in the space between the electrodes 70, 74, the capacitance of the capacitor 16 increases.

As shown in FIG. 6, the circuit comparator 59 provides an output of a train of pulses at a predetermined frequency. The pulse train is supplied through the matched diode pair 55 to two legs of the circuit. The upper leg of the circuit includes probe 14, and specifically electrodes 70 and 72 which form capacitor 16. The capacitance of the capacitor 16 varies depending upon whether water or glycol is present in the oil between the electrodes 70, 74. When water or glycol is not present in the oil, the output of the comparator 61 is high. When water or glycol is present in the oil, the output of the comparator 61 goes low and this low signal is supplied to the warning system from 51B. FIG. 7 illustrates the circuitry for the warning system. The output from the probe circuitry is J2-2. The left hand portion of the circuitry provides a power supply from the alternator of the vehicle. A comparator 99 is provided on the right hand side of the circuitry with am output passing through resistor R7 to a relay K1. When the output of J2-2 is at a predetermined level, the comparator 99 outputs a high signal and a loop around the comparator 99 which includes resistor R4 keeps the signal high. The signal from the comparator 99 is sent to the relay K1 which activates an inductor and closes a switch on the relay K1, which signals an operator that water or glycol is present in the oil system.

The dielectric constant of oil is about 1.8 and the dielectric constant of the water and glycol is known to be between 60 and 80. Due to this significant difference dielectrics constant, a substantial change in capacitance is effected by even small amounts of water/glycol between the electrodes 70, 74 of the probe 14. Contamination as low as 0.5% of water or glycol has been detected under experimental use of the present invention. The concentrator 12 separates minute quantities of water/glycol from oil in the system and concentrates the separated water/glycol into the region of the probe 14. In this manner, the probe 14 is capable of detecting the presence of water/glycol even when the concentration of contamination in the overall system is quite low. Some systems, such as those described in the aforementioned U.S. Pat. Nos. 4,624,779 and 4,995,992, may tolerate contamination in the fuel or oil system so long as it is efficiently separated prior to use. The present invention, however, is intended for use in systems in which even minute amounts of water/glycol contamination cannot be tolerated. In such systems, apart from the direct effects of the contamination, the presence of water/glycol in the oil system is likely to be an indicator of a more serious leak or other problem which must be repaired immediately in order to avoid catastrophic and expensive failure.

The present invention also provides a method for measuring the presence of water or glycol in an oil system using the sensor set forth above. According to the method, a concentrator 12 for concentrating water/glycol from an oil and water/glycol mixture is provided. The method includes passing oil and water/glycol mixture through the concentrator 12 such that the water/glycol is concentrated in a concentrating zone 84 of the concentrator. The method includes providing a water/glycol detection probe 14 and positioning the detection probe 14 in the concentrating zone 84. The detection probe 14 is operated to sense the presence of water/glycol in the concentrating zone 84. A warning system as described above, is provided. The detection probe 14 signals the warning system when the detection probe 14 indicates the presence of water or glycol in the system.

The present invention provides an efficient sensor for detecting the presence of water or glycol in oil. By the unique combination of the use of a probe 14 which is located in a water/glycol concentrating zone 84 of a concentrator 12, the presence of water or glycol may be detected at very low contamination levels. This early detection provides an early warning of a contaminated system which may mitigate the need for costly repairs.

The illustrated embodiment is an example of the invention. Many changes and adaptations may be made to the above-described embodiments without departing from the spirit and scope of the invention. For example, an apparatus for sensing the contamination of oil with a probe which measures the resistance of water/glycol in a concentrating zone of a water/glycol concentrator would be considered equivalent to the preferred mode of the present invention, as set forth above.

Patent protection is not to be determined by the illustrated embodiment, but rather by the claims which follow, construed by use of the established rules of patent claim construction, including use of the doctrine of equivalents.

What is claimed is:

1. An apparatus for early detection of the presence of minute quantities of contaminant in oil, said contaminant including at least one of water and glycol, comprising:

separator means through which oil is circulated for concentrating contaminant from contaminated oil in a designated concentration zone;

a contaminant detection probe means positioned in the concentrating zone and including capacitor means for sensing the capacitance of contaminant in oil in the concentration zone, the capacitance of the capacitor means being a function of the amount of contaminant in the oil; and means responsive to the capacitance sensed by the capacitor means for signaling the presence of contaminant in the oil.

2. The apparatus of claim 1, wherein said responsive means comprises a comparitor circuit to monitor the capacitance of the capacitor means, and further includes a warning system, said warning system signaling an increase in capacitance of the capacitor when said contaminant is present in the concentrating zone.

3. A method for sensing the presence of a contaminant in an oil system, said contaminant including at least one of water and glycol, comprising the steps of:

providing means for concentrating said contaminant from contaminated oil;

passing said contaminated oil through said concentrator means such that the contaminant is concentrated in a designated concentration zone;

providing a contaminant detection probe means including capacitor means for sensing a capacitance of said contaminant in oil; and positioning said detection probe means in said concentration zone, whereby said capacitance is a function of the amount of contaminant in the oil such that the detection probe means will sense the presence of the contaminant in the concentration zone prior to the concentration of contaminant in said oil system reaching an otherwise detectable level.

4. The method of claim 3, further comprising:

providing a warning system; and said detection probe means signaling said warning system when the detection probe means senses the presence of contaminant in the oil system.

\* \* \* \* \*